United States Patent [19]
Krauter et al.

[11] Patent Number: 5,464,007
[45] Date of Patent: Nov. 7, 1995

[54] FLUID INSENSITIVE BRAKING FOR AN ENDOSCOPE

[75] Inventors: Allan I. Krauter, Syracuse; Robert L. Vivenzio, Auburn; Michael P. Kehoskie, Jordan, all of N.Y.

[73] Assignee: Welch Allyn, Inc., Skaneateles Falls, N.Y.

[21] Appl. No.: 200,383

[22] Filed: Feb. 23, 1994

[51] Int. Cl.[6] ........................................ A61B 1/00
[52] U.S. Cl. .................... 600/144; 600/148; 600/149
[58] Field of Search ........................... 128/4, 6; 138/120; 403/358, 359, 326, 328

[56] References Cited

U.S. PATENT DOCUMENTS

| | | |
|---|---|---|
| 4,207,873 | 6/1980 | Kruy . |
| 4,461,282 | 7/1984 | Ouchi et al. . |
| 4,539,586 | 9/1985 | Danna et al. . |
| 4,617,914 | 10/1986 | Ueda . |
| 4,742,816 | 5/1988 | Suzuki et al. . |
| 4,825,850 | 5/1989 | Opie et al. ................... 128/4 |
| 5,007,406 | 4/1991 | Takahashi et al. ........... 128/4 |
| 5,014,685 | 5/1991 | Takahashi ..................... 128/4 |
| 5,329,887 | 7/1994 | Ailinger et al. .............. 128/4 |

Primary Examiner—Richard J. Apley
Assistant Examiner—Beverly M. Flanagan
Attorney, Agent, or Firm—Harris Beach & Wilcox

[57] ABSTRACT

A fluid insensitive system for braking the displacement cables of an endoscopic insertion tube wherein at least one control wheel is mounted on the outside of the insertion tube control housing. A brake disc is slidably mounted adjacent the control wheel and is moved in and out of engagement with the wheel by an actuator. A ratchet mechanism acts between the control wheel and the brake disc to apply a restraining force against the wheel when the wheel and the brake disc are in engagement.

25 Claims, 9 Drawing Sheets

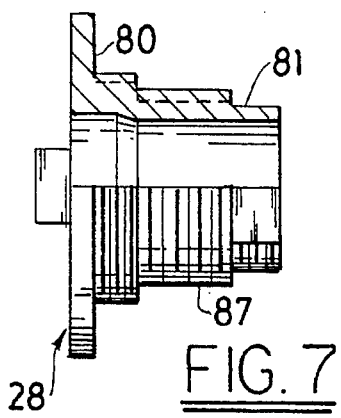
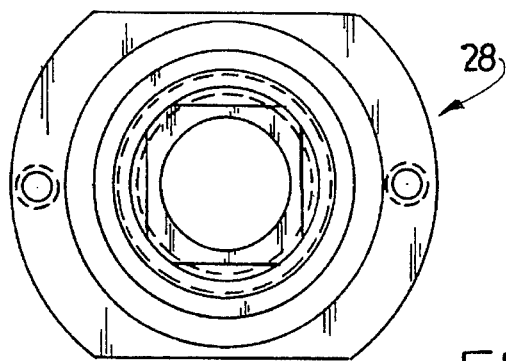
FIG. 7     FIG. 8
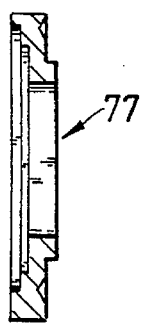
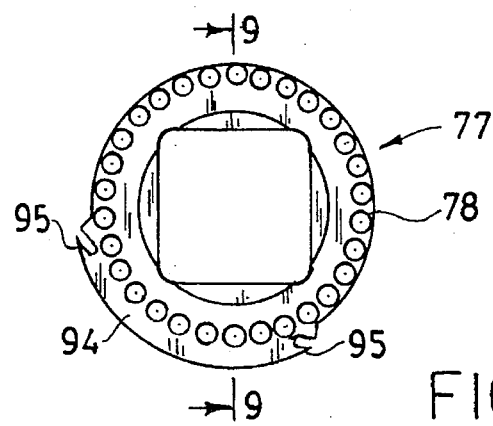
FIG. 9     FIG. 10
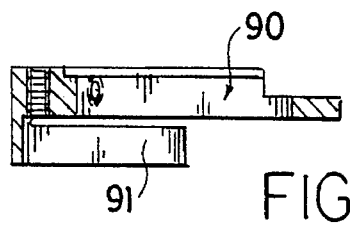
FIG. 13
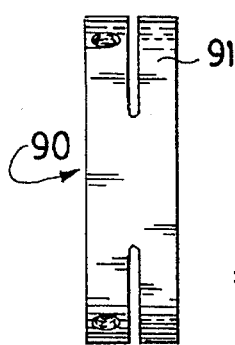
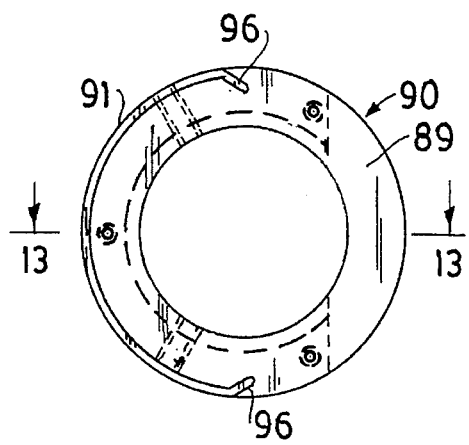
FIG. 11     FIG. 12

FLUID INSENSITIVE BRAKING FOR AN ENDOSCOPE

BACKGROUND OF THE INVENTION

This invention relates generally to endoscopy and, in particular, to a fluid insensitive braking system for use in endoscopes.

The term endoscope shall be used herein in a generic sense to include broadly endoscopes, borescopes, and guide tubes. In many endoscopes the distal end of the insertion tube is capable of being articulated by a steering mechanism that includes a pair of external control wheels coupled to steering cables mounted inside the insertion tube. Rotation of one of the control wheels produces an up or down deflection of the distal tip of the insertion tube while rotation of the second control wheel produces a left or right deflection of the insertion tube tip. As can be seen, by operating the two control wheels, the distal end of the insertion tube can be pointed at a desired target within the range of the instrument or maneuvered through a tortuous path of travel.

The control wheels of the endoscope are typically affixed to superimposed shafts that are mounted on the control handle of the insertion tube. The shafts pass into the housing and are coupled to the steering cables by means of rack and pinion units or the like. It is necessary to apply a holding force to the steering cables in order to maintain the distal tip of the insertion tube at a desired fixed position. Heretofore this was generally achieved by friction pads that applied a friction force against some moving component of the steering section. Fluids, however, can lodge between a conventional brake pad and the moving component of the steering section which changes the frictional characteristics at the interface. A constant torque is needed which is high enough to hold the distal tip of the insertion tube at a desired target position yet low enough to allow the distal tip of the insertion tube to self straighten during withdrawal from a confining space. A constant braking force also provides the user with a definite "feel" for the controls which facilitates rapid and accurate positioning of the insertion tube.

In the case of a medical endoscope, it is extremely important that the insertion tube be immersable in a cleaning fluid for sanitary purposes. This heretofore requires that the friction brake surfaces be completely isolated by fluid tight seals to prevent the pad from becoming wet. It is extremely difficult to properly seal these areas, and oftentimes the seal will deteriorate or break in time with usage. The seals are also expensive to fabricate and maintain and, because of their complexity, can themselves create contamination sites that are hard to keep clean.

U.S. Pat. No. 4,207,873 to Kruy discloses a braking system for an endoscope in which the traditional friction pad brakes are replaced by an incrementing ring having spaced apart indentations formed about its periphery that coact with a pair of pawls mounted in the companion control wheel. Each pawl includes a spring loaded ball which is seated in a set screw that is threaded radially into the hub of the control wheel. The wheel is slidably mounted upon a control shaft adjacent to the incrementing ring which in turn, is affixed securely to the shaft. To actuate the brake, the wheel is moved axially into engagement with the incrementing ring. Each of the spring loaded balls must first snap over a retaining ring before being received in one of the indentations. Once engaged, the spring loaded detent ball places a prescribed holding force against the control wheel.

The incrementing rings and spring loaded balls of the Kruy system are mounted on the outside of the control handle and are thus open to the surrounding ambient. Consequently, the relatively sensitive detent springs acting on the detent balls are exposed to moisture that can find its way into the spring housing set screw and thus cause corrosion of the spring. Any deterioration of the springs will lead to a change in the force exerted upon the steering system. Cleaning of the confined area behind the detent wall is also difficult.

SUMMARY OF THE INVENTION

An object of the present invention is to improve braking system use in the steering mechanisms of endoscopes and borescopes.

A further object of the present invention is to provide an open braking system for the steering system of an endoscope which does not require seals and which can be efficiently cleaned without adversely affecting the operation of the brake.

A still further object of the present invention is to provide a braking system for an endoscope having an open construction that permits cleaning fluids to reach all parts of the brake system.

Yet another object of the present invention is to provide a fluid insensitive braking system for an endoscope.

These and other objects of the present invention are attained by means of a steering mechanism for the flexible insertion tube of an endoscope. The insertion tube contains an articulation section at its distal tip and deflection cables extending from the distal tip to the proximal end thereof. Control wheels are mounted upon the outside of a control housing which is located at the proximal end of the insertion tube. The control wheels are connected to the deflection cables and can be maneuvered to point the tip at a desired target. A brake disc is movably mounted adjacent to each control wheel member and is moved axially by an actuator toward and away from the control wheel. A ratchet mechanism acts between the brake disc and the control wheel to place a biasing force against the control wheel when the two are placed in engagement by the actuator.

BRIEF DESCRIPTION OF THE DRAWINGS

For a better understanding of these and other objects of the present invention, reference will be made to the following detailed description of the invention which is to be read in association with the accompanying drawings, wherein:

FIG. 7 is a side elevation of a hub for mounting the up/down control wheel upon the control housing;

FIG. 8 is an end view of the hub shown in FIG. 7;

FIG. 9 is a side view in section of the up/down brake disc;

FIG. 10 is a front view of the up/down brake disc;

FIGS. 11–13 are three views of the up/down brake actuator cover;

DETAILED DESCRIPTION OF THE INVENTION

Figure 1:
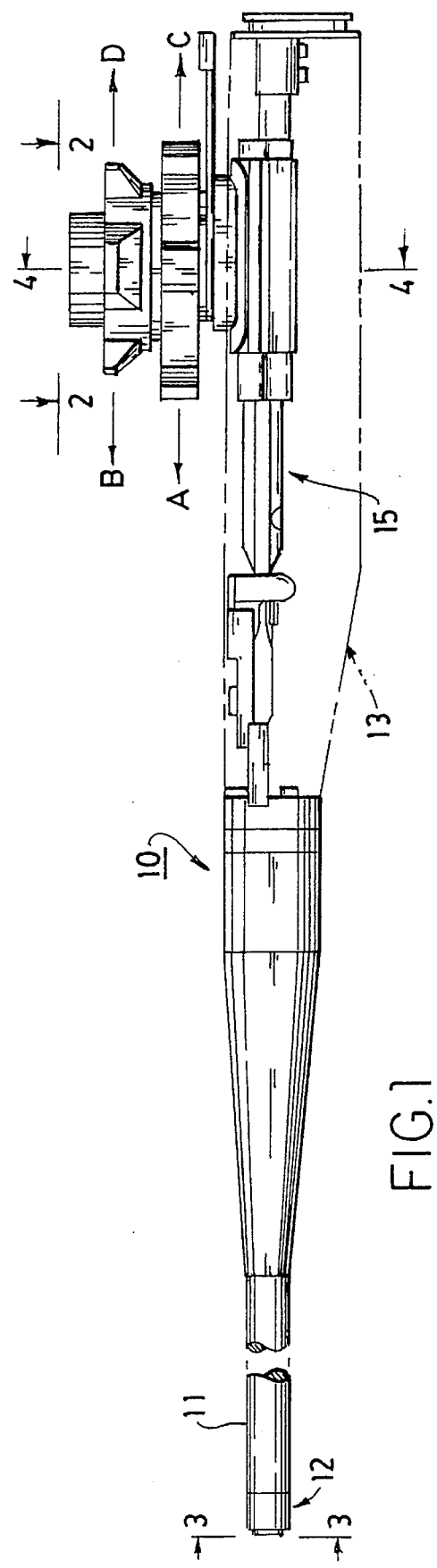
FIG. 1 is a partial side elevation of an endoscopic insertion tube with portions broken away to better illustrate the steering section thereof.
Figure 4:
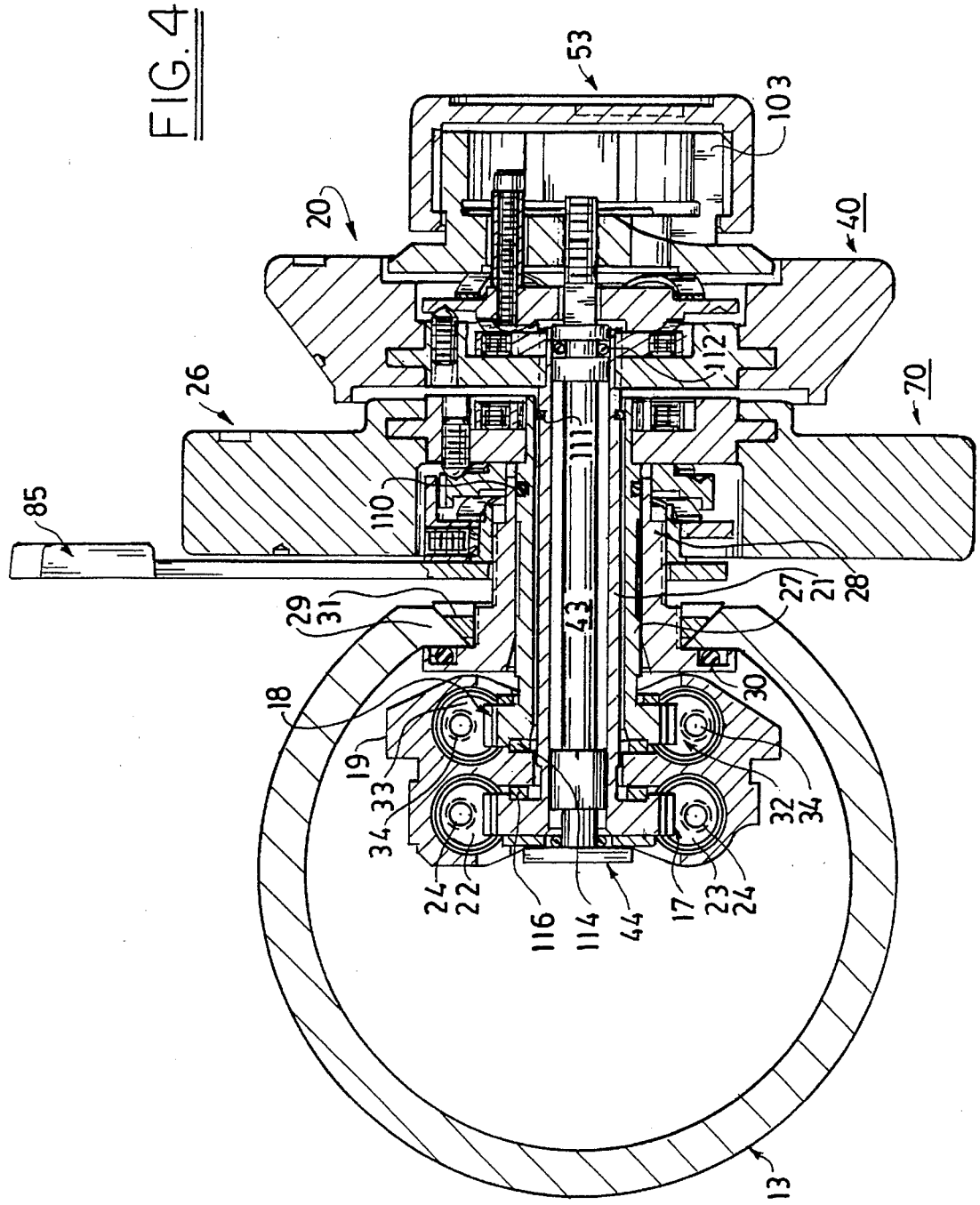
FIG. 4 is an enlarged sectional view taken along lines 4—4 in FIG. 1.

Referring now to FIG. 1, there is shown an insertion tube 10 of the type employed in a video endoscope. The distal end 11 of the insertion tube is equipped with viewing head 12 that contains a CCD solid state imager (not shown). The proximal end of the insertion tube contains a hand engageable control housing 13 that is shown in phantom outline in FIG. 1. Mounted inside the housing is a steering mechanism generally referenced 15. As best seen in FIG. 4, the steering mechanism includes a pair of rack and pinion units 17 and 18 that are attached to displacement cables for articulating the distal end of the insertion tube. The outer rack and pinion unit 17 is connected to a first left/right control wheel 20 by means of a hollow inner shaft 21. The racks 22 and 23 of the unit 17 are attached to displacement cables 24 so that rotation of the control wheel 20 in directions B and D (FIG. 2) will cause the distal end of the insertion tube to be bent in a horizontal plane either to the right or the left of the axial centerline of the insertion tube.

The inner rack and pinion unit 18 is connected to a second up-down control wheel 26 via a second hollow shaft 27 that is housed inside a cylindrical support member 28 which forms part of the housing frame 19. The support member passes outwardly through the side wall 29 of the control housing and the opening closed by seal 30 and by the housing attachment ring 31. Racks 32 and 33 of the inner rack and pinion unit 18 are connected to displacement cables 34 whereby rotation of the second larger diameter wheel 26 in the A or C (FIG. 2) direction produces an up or down bending movement of the distal end of the insertion tube in a vertical plane. As can be seen, by manipulating the two control wheels, the distal end of the insertion tube can be directed in an infinite number of positions.

Figure 3:
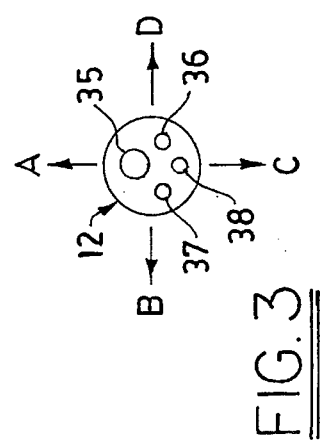
FIG. 3 is an end view of the distal tip of the insertion tube taken along lines 3—3 in FIG. 1.

As shown in FIG. 3, the viewing head 12 is mounted at the distal tip of the insertion tube and contains an optical window 35 through which the CCD imager can view a target within the range of the viewing optics. Light is directed onto the target area by means of a pair of fiber bundles 36 and 37 situated on either side of the viewing window. A biopsy channel 38 also opens to the target region through the front face of the distal tip and permits instruments to be inserted therethrough to carry out various well-known procedures. As noted above, by manipulating the control wheels, the front face at the distal tip of the insertion tube can be pointed accurately at a target located in a remote and generally inaccessible region or the tube can be guided through tortuous passages.

Figure 2:
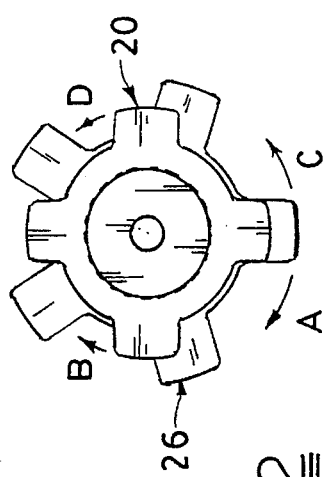
FIG. 2 is a top view showing the control wheels that are mounted upon the control handle of the insertion tube.

The left/right control wheel 20 is placed on the outside of the up/down control wheel 26. As illustrated in FIG. 2, the wheels each have a different size diameter and the geometry of the wheels is also different. The outer wheel is smaller in diameter and contains four radially disposed spokes while the inner wheel has a larger diameter and contains five equally spaced spokes extending radially from the hub of the wheel. A person using the endoscope can rapidly identify each wheel by touch, thus allowing the user to continually view the target region on the video screen (not shown) to which the CCD imager is electrically connected.

With further reference to FIGS. 22–28 there is shown a sub assembly of the left/right control wheel system generally referenced 40. The sub assembly includes the previously noted left/right control wheel 20 which is secured to the hollow shaft 21 for rotation therewith. A pinion 41 is mounted on the inboard end of the shaft and mates with the rack 22 and 23 of the outer rack and pinion unit 17 (FIG. 4). A stationary support shaft 43 is contained within the hollow shaft 21 and is secured to the housing frame 19 by means of an end bracket 44. The shaft 21 is rotatably mounted upon the support shaft by means of bearings 45 and 46 whereupon the left/right control shaft can be freely rotated by turning the control in either direction B or D as seen in FIG. 2. In assembly, the control wheel is mounted on a square section 47 at the end of the hollow shaft 21 and is tightened against a shoulder 48 formed on the shaft. The wheel is held tightly against the shoulder by means of a jam nut 49 that is threaded onto the shaft behind the wheel and tightened against the end face of the wheel hub 50. Set screws 51—51 are threaded through the jam nut and are tightened down against the hub to further secure the wheel to the shaft.

The right end of the support shaft 43 is equipped with a threaded shank 52 upon which an actuator knob 53 is mounted. Turning the actuator knob upon the shank causes the knob to move axially toward or away from the inner end face of the left/right control wheel hub 50. A floating brake disc 55 (FIGS. 26 and 27) having a square shaped centrally located hole 57 is mounted on a square section 56 of the support shaft 43 (FIGS. 24 and 25) so that the brake disc can move axially between the actuator knob and the hub of the left/right control wheel. The threaded shank of the support shaft is provided with a multiple thread whereby turning of the actuator knob will produce rapid axial movement of the knob toward or away from the control wheel 20.

A pair of wave washer springs are mounted on either side of the brake disc 55. The spring rate of wave washer 59 is greater than that of wave washer 60, the reason for which will be explained in greater detail below. In practice, each of these wave washers can consist of several stacked individual wave washers.

A ratchet mechanism is made up of detent pins 62 (preferably three) and a series of circumferentially spaced depressions 63—63 formed in the face of the brake face that is adjacent to the control wheel. The detent pins are staked into the hub of the control wheel and each has a rounded tip that is receivable into the circumferentially spaced depressions formed in the brake disc. Turning the actuating knob in one direction will cause the wave washer springs to be compressed and will force the brake disc into engaging contact with the detent pins, thus placing a biasing force upon the ratchet mechanism. This in turn places a braking torque upon the control wheel and a braking force on the associated displacement cable. The torque needed to do this depends on the net axial engagement force of the two springs, the geometry of the detent pin tips and the receiving depressions, the radial location of the depressions, and to a much lesser extent, upon the friction coefficient of the sliding surfaces of the ratchet mechanism. The braking torque achieved can be varied by changing the axial travel of the actuating knob and/or by changing the relative stiffness of the springs.

Figure 23:
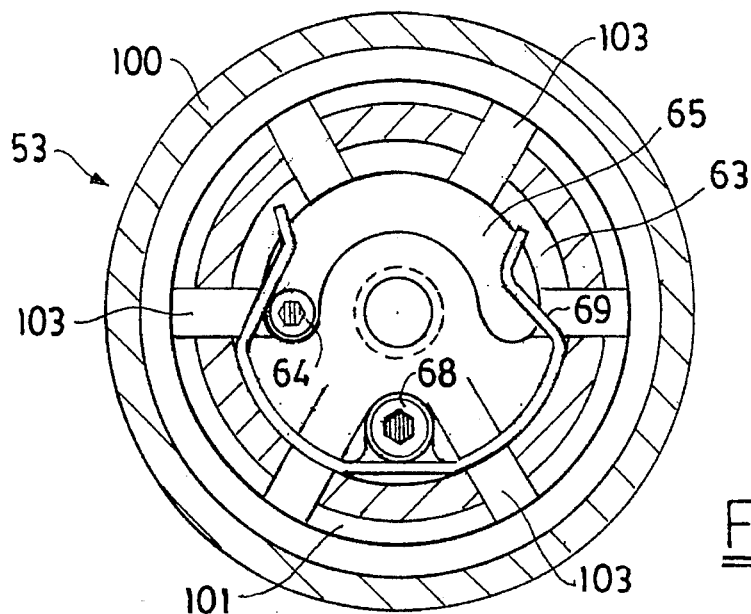
FIG. 23 is a sectional view taken along lines 23—23 in FIG. 22.
Figure 24:
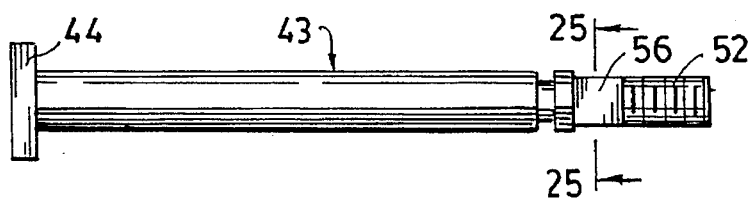
FIGS. 24 and 25 are two views of the left/right control wheel shaft.
Figure 25:
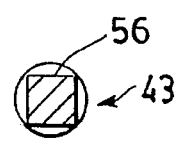
Figure 26:
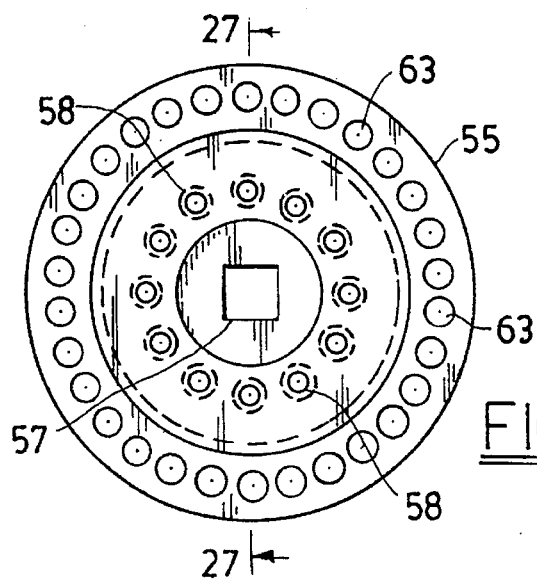
FIGS. 26 and 27 are two views of the left/right brake disc.
Figure 27:
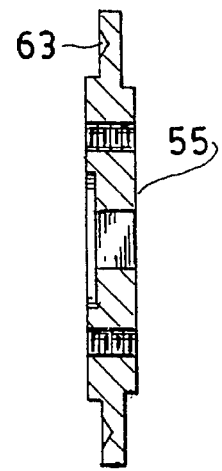
Figure 28:
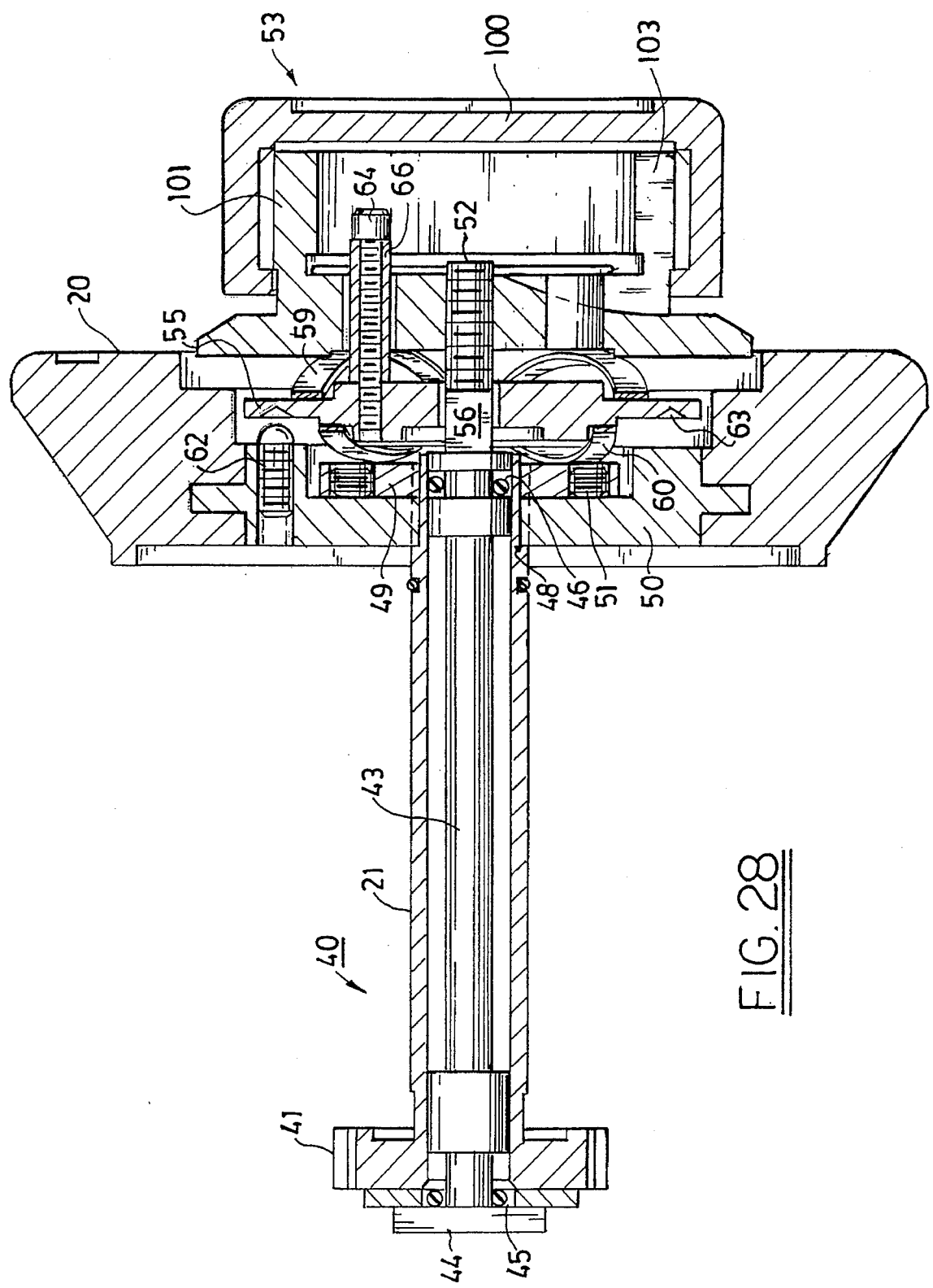
FIG. 28 is a sectional view similar to that of FIG. 22 showing the left/right brake disc in a disengaged position.

Turning now to FIG. 23, there is shown a stop mechanism 63 for regulating the amount of axial travel afforded the actuator knob. The stop mechanism includes an axially disposed stud 64 which is threaded into one of a series of threaded holes 58—58 formed in the brake disc (FIG. 26). The stud is arranged to pass upwardly through an arcuate shaped slotted hole 65 formed in the hub of the actuator knob. A cylindrical sleeve 66 surrounds the stud 64 (FIG. 28). The slotted hole subtends an arc of about 180° thus permitting the knob to be advanced or retracted freely along the threaded shank of the support shaft about one-half a turn. A spring 69 is mounted in the hub of the actuator knob and is contoured to hold the stud in the extreme brake disc engaging and disengaging positions against the end walls of the slotted hole. The spring is attached to the actuator knob by screw 68.

When the stud is bottomed against one end wall of the slotted hole, the actuator knob is retracted to the position shown in FIG. 28 and the compressive force on spring 59 is relieved. The softer spring 60 will now take over and push the brake disc away from the control wheel hub, thus disengaging the ratchet mechanism. This allows the control wheel to turn freely and smoothly during the steering operation. Turning the actuator knob in the opposite direction will bring the stud against the other end wall of the slotted hole, thus compressing the spring 59 and producing an engagement of the ratchet as explained above. At this time, the spring 59 acting through the ratchet mechanism will place a braking force against the left/right control wheel thus holding the distal tip of the insertion tube at a desired position in the horizontal plane. The control wheel can be incremented in either direction between the depressions in the brake disc by applying sufficient torque to the wheel to overcome the spring holding force.

Figure 21:
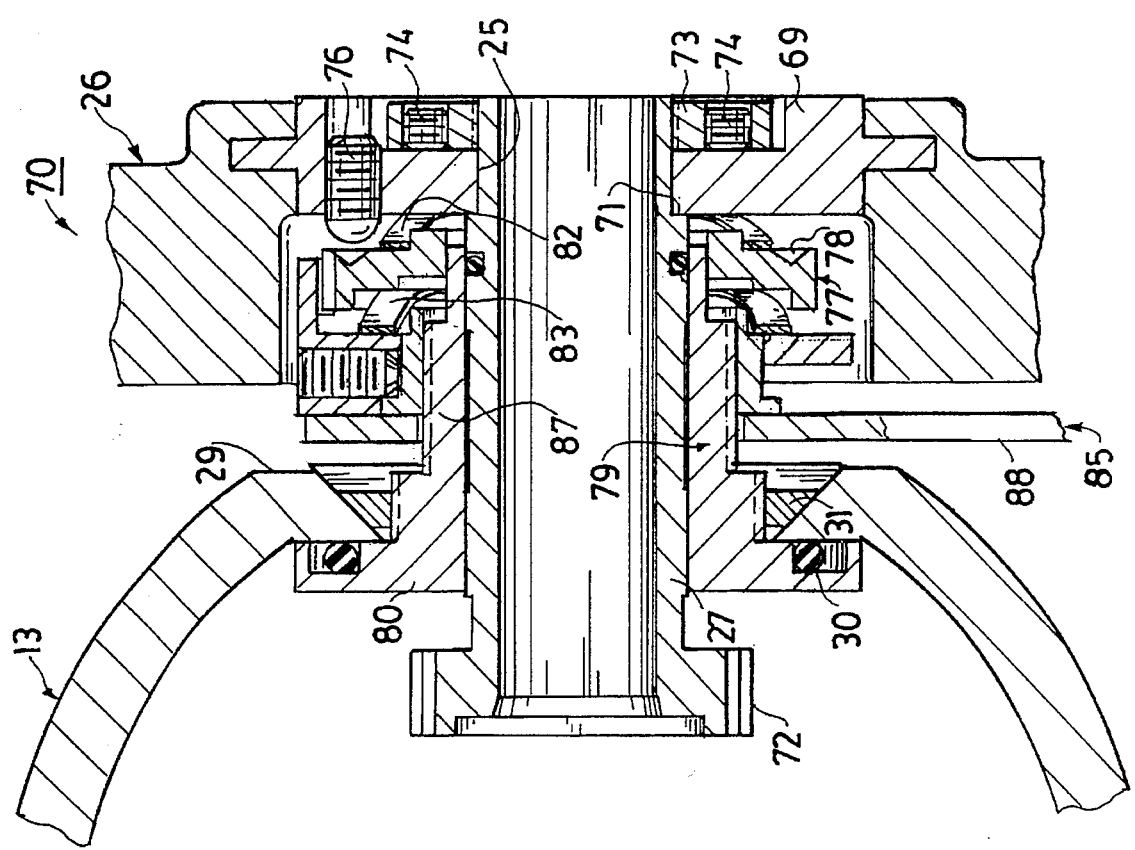
FIG. 21 is a sectional view similar to that of FIG. 5 showing the up/down brake disc in a disengaged position away from the adjacent up/down control wheel.
Figure 22:
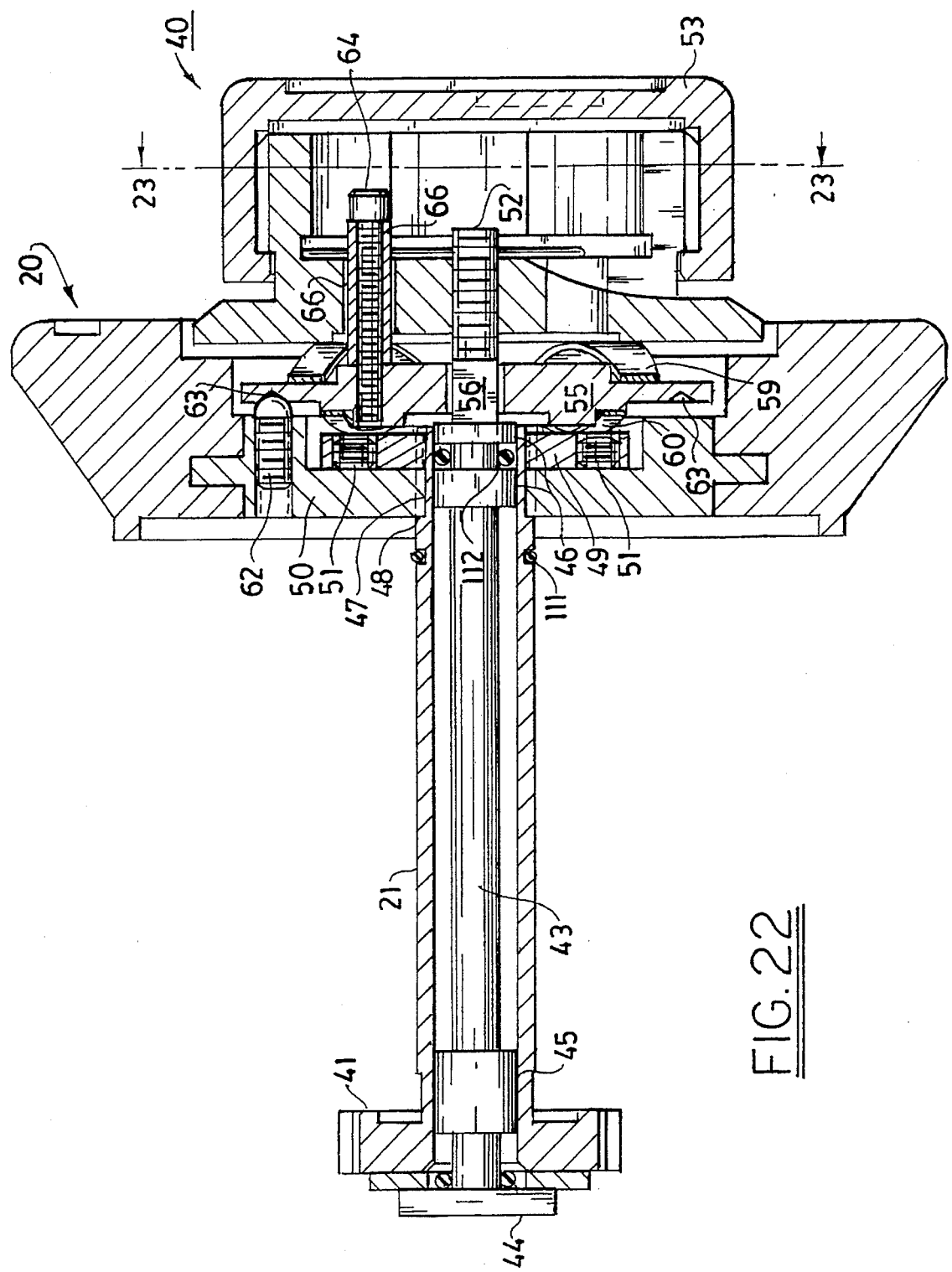
FIG. 22 is a side elevation in section showing the left/right control wheel and an associated brake disc in engagement with the adjacent control wheel.

With further reference to FIGS. 5–21 there is shown the sub assembly of the up/down control system which is generally referenced 70 (FIG. 21). The up/down control system operates in much the same manner as the left/right control system to apply a braking torque to the steering mechanism and thus hold the distal end of the insertion tube in a desired position in a vertical plane. The up/down control wheel 26 is secured for rotation to a square section 25 at the end of the hollow shaft 27 that surrounds the previously noted left/right control shaft 21. A pinion 72 is mounted on the inner end of the shaft and, as explained above, is arranged to engage a pair of racks for moving the up/down displacement cable 34 (FIG. 4) contained within the insertion tube. The control wheel is mounted on the outer end of the shaft and is tightened against a raised shoulder 71 from on the shaft. A jam nut 73 is threaded onto the shaft behind the hub of the control wheel to lock the hub against the shoulder. Set screws 74—74 are used to hold the jam nut securely against the control wheel in assembly.

Three detent pins 76 are staked into the hub 69 of the control wheel and extend inwardly from the hub toward the up/down brake disc 77. A series of circumferentially spaced depressions 78—78 are formed in the front face of the brake disc for receiving the contoured tips of the detent pins 76.

A cylindrical support member 28 surrounds the up/down control shaft. The support member is equipped with a radially expanded mounting flange 80 that is secured to the inside wall of the control housing by the housing attachment ring 31. The main body section of the support cylinder passes out of the housing through an opening in the housing side wall.

Figure 6:
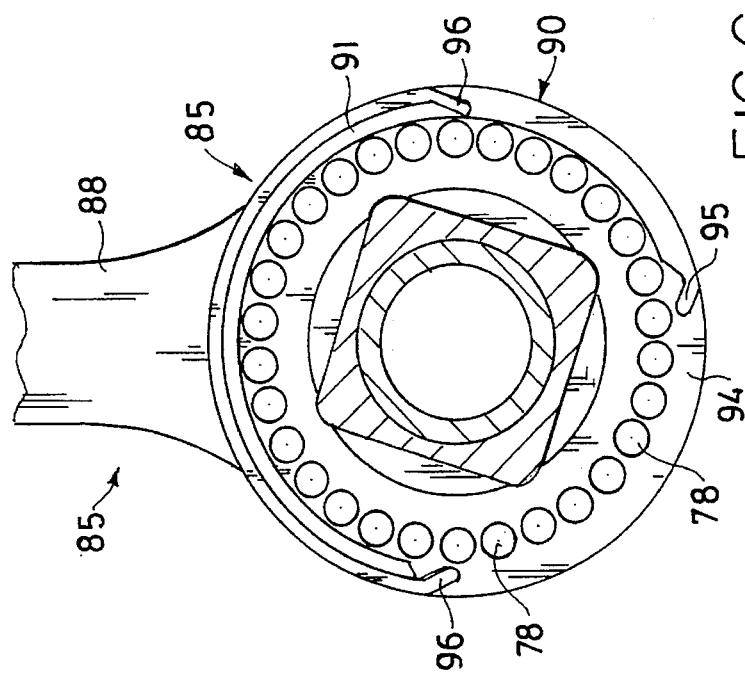
FIG. 6 is a sectional view taken along lines 6—6 in FIG. 5.

The up/down brake disc 77 is slidably mounted on a flat section 81 (FIG. 7) of the support cylinder so that it can move axially toward and away from the hub of the up/down control wheel 26. A pair of wave washer springs 82 and 83 are positioned on either side of the brake disc. Spring 82 has a lower spring rate than spring 83 and is positioned between one face of the brake disc and the hub 69 of the control wheel 26. The other (heavier) spring 83 is positioned between the disc and an actuator unit generally referenced 85 (FIG. 6). In practice, each of these wave washer springs can consist of several stacked individual wave washers.

As best seen with reference to FIGS. 6–20, the actuator unit 85 includes a cylindrical hub 86 (FIG. 14) having internal threads that permit the hub to be screwed onto the threaded section 87 (FIG. 7) on the support member 28. A lever arm 88 (FIG. 6) is secured to the front face 89 (FIG. 12) of a shroud 90 to clamp the hub therebetween. A yoke 91 which forms part of the shroud extends outwardly from the shroud. In assembly, the yoke overlies and partially encompasses the up/down brake disc.

As best illustrated in FIGS. 9 and 10, the brake disc 77 has a radially extended section 94 that contains a pair of slots 95 situated at each end of the radially extended section 94. The slots are adapted to receive therein tabs 96—96 that are carried on the circumferentially opposed ends of the shroud (FIG. 12).

Figure 5:
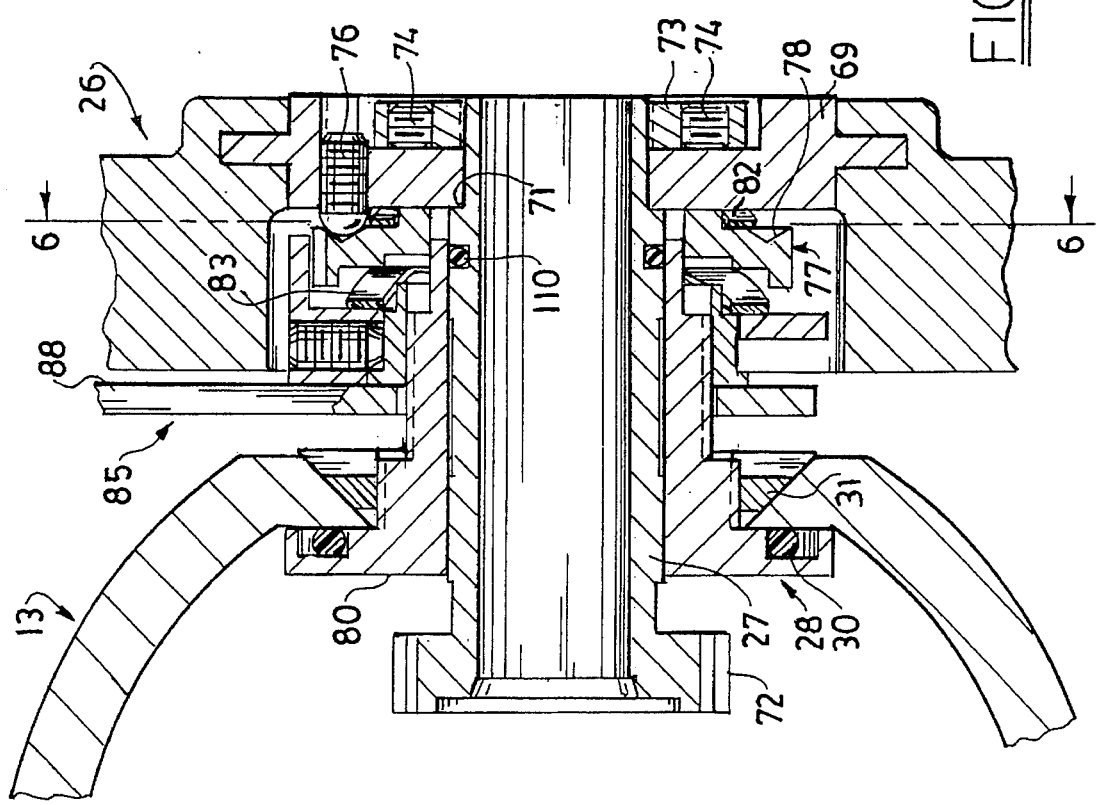
FIG. 5 is a further enlarged sectional view showing the up/down control wheel and a brake disc associated therewith in a control wheel engaging position.
Figure 14:
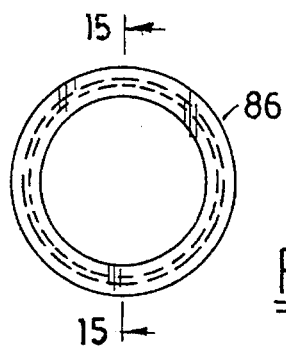
FIGS. 14 and 15 are two views of the up/down brake actuator arm hub.
Figure 15:
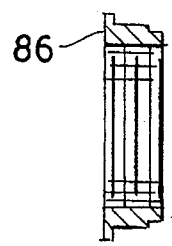
Figure 16:
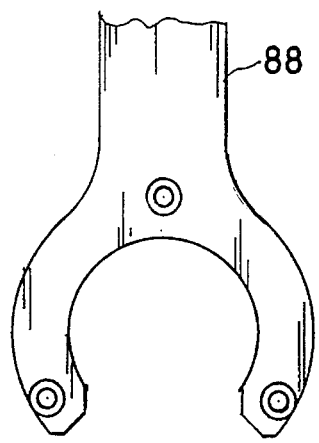
FIGS. 16 and 17 are two views showing the up/down actuator arm.
Figure 17:
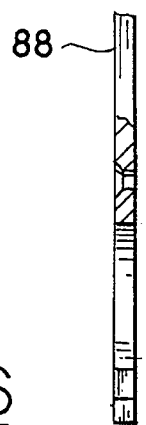
Figure 18:
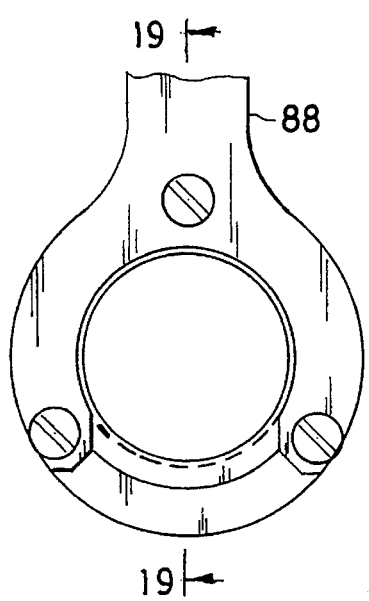
FIGS. 18–20 are three views showing the up/down brake actuator arm assembly.
Figure 19:
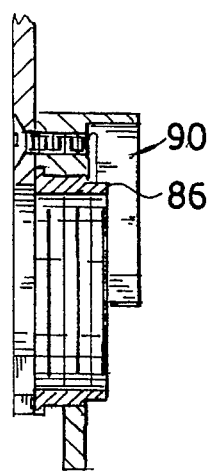
Figure 20:
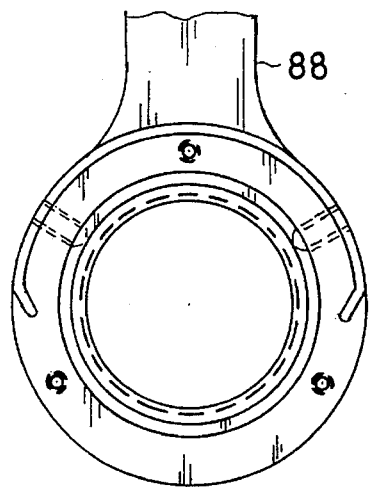

In operation, turning the lever arm will cause the actuator unit to move axially toward or away from the control wheel 26 (FIG. 5 and FIG. 21). The amount of rotation afforded the actuator unit is regulated by the circumferential spacing between the two slots formed in the brake disc. Turning the lever in one direction so that a tab on the shroud seats in one slot will advance the actuator unit toward the up/down control wheel thus compressing the springs 82 and 83 (FIG. 5). This, in turn, will cause the depressions 78 formed in the brake disk to be seated on the pins 76, thus placing a restraining force on the up/down deflection cable. As in the case of the left/right control system subassembly, rotation of the control wheel occurs when the applied torque is sufficient to overcome the spring pressure holding the detent pins in the depressions. Accordingly, the deflection cable can be incremented in either direction by moving the pins between adjacent depressions.

Rotating the lever arm in the opposite direction will cause the actuator unit to move away from the control wheel (FIG. 21). The pressure on the heavy spring 83 is released and the softer spring is now allowed to push the brake disc away from the detent pins, thus disengaging the ratchet mechanism. With the ratchet disengaged, the up/down control wheel is able to move freely.

With further reference to FIGS. 23 and 28, actuator knob 53 includes an outer cylindrical cap 100 that is press fitted upon an inner rotor 101 which is in turn threaded upon the outer end of support shaft 43. A series of spaced apart drain channels 103 are formed in the raised side wall of the rotor that allow any fluid trapped under the cap 100 to efficiently drain from beneath the knob thus rendering this region fluid free in the event the instrument is exposed to cleansing fluids or the like.

As depicted in FIG. 4, the present control knob assembly, because of its fluid insensitive brake system, is able to utilize a very simple sealing arrangement to prevent cleansing fluids and the like from entering the control housing 13 of the instrument when compared to other endoscopic braking systems. As shown in FIG. 4, the sealing arrangement includes an O-ring seal 30 that acts between the support member 28 and the inner wall of the control housing. A series of two further O-rings 110 and 111 are mounted along the two pinion shafts 21 and 27 and finally an end O-ring seal 112 is mounted between the support shaft and inner shaft 21. Seals 110–112 prevent fluids from entering the control housing from between the shafts.

The inner shaft O-ring 111, under certain conditions, may transmit torque between the pinion shafts 21 and 27. As a result, rotation of one shaft may tend to cause the other shaft to rotate also. This can be avoided by eliminating O-ring 111 and, instead, placing an O-ring 114 between the inboard end of shaft 27 and the housing frame 19 and another O-ring 116 between the inboard end of shaft 21 and the housing frame 19.

As should now be evident, the apparatus of the present invention provides a braking system for the endoscope that is insensitive to fluids, such as cleaning fluids or the like, to which this type of instrument is exposed. It should be further noted, because of the arrangement of the present control and braking system, it can be securely mounted upon the control housing of the insertion tube of an endoscope employing a minimum number of seals. The overall construction of the control and braking system is thus greatly simplified without sacrificing reliability or efficiency of operation.

While this invention has been explained with reference to the structure disclosed herein, it is not confined to the details set forth and this invention is intended to cover any modifications and changes as may come within the scope of the following claims:

What is claimed is:

1. A steering mechanism for a flexible insertion tube of an endoscope having an articulation section at its distal end and deflection cable means extending from the distal end to a proximal end thereof, said steering mechanism comprising;

a control housing operatively connected to the proximal end of said insertion tube;

a control wheel mounted for rotation on the exterior of said control housing;

connecting means for coupling said control wheel to a deflection cable for articulating the distal end of said insertion tube;

brake means movably mounted adjacent to said control wheel;

actuating means for moving the brake means between a first position wherein the brake means is out of engagement with said control wheel and a second position wherein said brake means is in braking engagement with said control wheel coacting means in the control wheel and the brake means for rotationally incrementing said control wheel when the brake means is in said second position, and biasing means for applying force against the brake means when said brake means is in said second position for applying a holding force against the control wheel.

2. The steering mechanism according to of claim 1 further including spring means for urging said brake means out of engagement with said control wheel when said actuator means is in said first position.

3. The steering mechanism according to claim 2 wherein said biasing means and said spring means are wave washers positioned on either side of said brake disc means.

4. The steering mechanism according to claim 1 wherein said connecting means includes rotatable shaft means secured to a subcontrol wheel and arranged to turn with said control wheel.

5. The steering mechanism according to claim 4 further including a fixed member axially aligned with said rotatable shaft means and said brake means being slidable in an axial direction into and out of engagement with said control wheel.

6. The steering mechanism according to claim 5 wherein said fixed member has a square section upon which said brake means is slidably mounted.

7. The steering mechanism according to claim 5 wherein said fixed member is attached to said control housing.

8. The steering mechanism according to claim 1 wherein an end face of said brake means is mounted opposite an adjacent end face of said control wheel and said coacting means includes at least one detent pin mounted in one of the end faces that is arranged to engage circumferentially spaced depressions formed in said adjacent end face whereby said control wheel can be rotationally incremented between depressions when said actuating means is in said second position.

9. The steering mechanism according to claim 8 wherein said fixed member has a threaded section and said actuating means is mated with said threaded section whereby turning said actuating means upon said threaded section will move the actuating means toward and away from said the control wheel.

10. The steering mechanism according to claim 9 wherein the threaded section contains multiple lead threads.

11. The steering mechanism according to claim 9 further including stop means associated with said actuator means, said stop means for limiting the amount of rotation afforded said actuator means.

12. A steering mechanism for a flexible insertion tube of an endoscope that has an articulation section at its distal end and deflection cable means extending from the distal end to a proximal end thereof, said steering mechanism comprising:

a control housing connected to said insertion tube at the proximal end thereof;

first and second control wheels mounted for rotation upon the exterior of said control housing;

connecting means for coupling said first control wheel to a first deflection cable for moving said distal end of the insertion tube in a vertical plane and coupling said second control wheel to a second deflection cable for moving said distal end of the insertion tube in a horizontal plane;

a brake disc means mounted exterior said control housing adjacent to each of said control wheels, said brake disc means being movable axially toward and away from said adjacent control wheel;

actuator means associated with each brake disc means for moving the brake disc means into a first engaging position wherein said brake disc means is disengaging with an associated control wheel and a second engaging position wherein the brake disc means is in engagement with said associated control wheel;

biasing means associated with each brake disc means for holding the brake disc means in engagement with said adjacent control wheel when said actuator means is in said second engaging position; and spring means associated with each brake disc means for urging the brake disc means out of engagement with the associated control wheel when the actuator means is in said first disengaging position.

13. The steering mechanism according to claim 13 wherein said biasing means and said spring means associated with each brake disc means includes at least one wave washer positioned on either side of the brake disc means.

14. The steering mechanism according to claim 11 wherein said connecting means includes shaft means secured to each of said first and second control wheels so that said shaft means turns with each control wheel.

15. The steering mechanism of according to claim 14 wherein said shaft means includes an inner shaft and an outer shaft surrounding said inner shaft.

16. The steering mechanism according to claim 15 further including first cylindrical support means encircling a portion of said outer shaft and second support means passing axially through said inner shaft, said first and second support means being secured to said control housing.

17. The steering mechanism according to claim 16 further including shaft sealing means acting between said first and second support means and the inner and outer shaft, and support sealing means acting between said first support means and said control housing.

18. The steering mechanism according to claim 16 wherein said second support means extends axially beyond an outer end of the inner shaft to provide an end section for supporting a respective brake means and a respective control wheel thereon.

19. The steering mechanism according to claim 18 wherein each of said first and second support means has a square cross-sectional section for slidably supporting a respective disc brake means thereon.

20. The steering mechanism according to claim 19 wherein one end face of each brake disc means is positioned opposite an adjacent end face of an associated control wheel and said coacting means includes at least one detent pin mounted in one of the end faces and circumferentially spaced depressions formed in the other end face for receiving a tip of said at least one detent pin therein when said actuator means is in said engaging second position.

21. The steering mechanism according to claim 20 wherein each of said first and second support means has a threaded section and said associated actuator means is threaded thereupon whereby turning said actuator means will move the brake disc means into and out of engagement with the associated brake disc means.

22. The steering mechanism according to claim 21 wherein said threaded sections contain multiple lead threads.

23. The steering mechanism according to claim 12 wherein each of said actuator means further includes a stop means for stopping said actuator means in said first engaging position and a second disengaging position.

24. The steering mechanism according to claim 23 wherein said actuator means further includes detent means for holding said actuator means in said first engaging position and in said second disengaging position and for permitting a user to feel engagement into said first position and disengagement into said second position.

25. The steering mechanism according to claim 12 further including drain means associated with at least one of said actuator means, said drain means for allowing fluids to drain away from said actuator means.

\* \* \* \* \*